United States Patent

Patsch et al.

Patent Number: 5,491,232
Date of Patent: Feb. 13, 1996

[54] SULFUR COMPOUNDS USEFUL FOR PREPARATION OF DYES

[75] Inventors: Manfred Patsch, Wachenheim; Ernst Schefczik, Ludwigshafen, both of Germany

[73] Assignee: BASF Aktiengesellschaft, Ludwigshafen, Germany

[21] Appl. No.: 423,849

[22] Filed: Apr. 18, 1995

[30] Foreign Application Priority Data

Apr. 28, 1994 [DE] Germany .............. 44 14 880.1

[51] Int. Cl.⁶ .................. C07D 279/02; C07D 209/48
[52] U.S. Cl. .............. 544/3; 546/142; 548/210; 548/472; 548/475; 548/478; 548/479
[58] Field of Search ............... 548/210, 472, 548/475, 478, 479; 546/142; 544/3

[56] References Cited

U.S. PATENT DOCUMENTS 3,489,766   1/1970   Weil et al. ............... 549/478
5,275,916   1/1994   Kato ...................... 430/286

Primary Examiner—Jacqueline Haley
Attorney, Agent, or Firm—Oblon, Spivak, McClelland, Maier & Neustadt

[57] ABSTRACT

Sulfur compounds of the formula

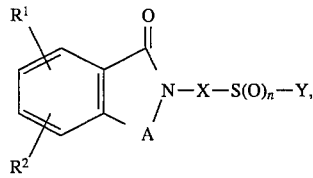

where
n is 0 or 2,
$R^1$ and $R^2$ are hydrogen, $C_1$–$C_6$-alkyl, $C_1$–$C_6$-alkoxy, halogen, nitro, amino, hydroxysulfonyl, $C_1$–$C_6$-alkoxycarbonyl or unsubstituted or substituted carbamoyl,
A is methylene, carbonyl, sulfonyl or a radical of the formula $CH_2$—CO or $CH_2$—$SO_2$,
is a direct bond or unsubstituted or substituted $C_1$–$C_8$-alkylene and
Y is vinyl or a radical of the formula $C_2H_4Q$, where Q is hydroxyl or a group which can be removed under alkaline reaction conditions,
and a process for their preparation are described.

4 Claims, No Drawings

SULFUR COMPOUNDS USEFUL FOR PREPARATION OF DYES

The present invention relates to novel sulfur compounds of the formula I

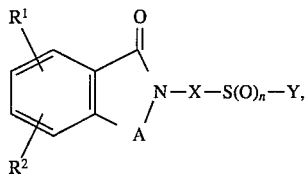

where
n is 0 or 2,
$R^1$ and $R^2$ independently of one another in each case are hydrogen, $C_1$-$C_6$-alkyl, $C_1$-$C_6$-alkoxy, halogen, nitro, amino, hydroxysulfonyl, $C_1$-$C_6$-alkoxycarbonyl, carbamoyl or $C_1$-$C_6$-mono- or dialkylcarbamoyl,
A is methylene, carbonyl, sulfonyl or a radical of the formula $CH_2$—CO or $CH_2$—$SO_2$, the methylene group in each case being linked to the benzene ring,
X is a direct bond, $C_1$-$C_8$-alkylene which may be interrupted by 1 to 3 oxygen atoms in ether linkage, 1 to 3 imino groups or 1 to 3 $C_1$-$C_4$-alkylimino groups, or a radical of the formula $L^1$—CO—$NR^3$—$L^2$, where $L^1$ and $L^2$ independently of one another in each case are $C_1$-$C_4$-alkylene and $R^3$ is hydrogen, $C_1$-$C_4$-alkyl or phenyl, and
Y is vinyl or a radical of the formula $C_2H_4Q$, where Q is hydroxyl or a group which can be removed under alkaline reaction conditions,
and a process for their preparation.

It is an object of the present invention to provide novel sulfur compounds which have a benzamide structural moiety. The novel substances are intended to be advantageously suitable for the preparation of dyestuffs.

We have now found that this object is achieved by the sulfur compounds of the formula I characterized in greater detail at the outset.

All alkyl and alkylene groups occurring in the abovementioned formula can be either straight-chain or branched.

$R^1$ $R^2$ and $R^3$ are e.g. methyl, ethyl, propyl, isopropyl, butyl, isobutyl, sec-butyl or tert-butyl.

$R^1$ and $R^2$ are furthermore e.g. pentyl, isopentyl, neopentyl, tert-pentyl, hexyl, 2-methylpentyl, methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, 2methylpentyloxy, methoxycarbonyl, ethoxycarbonyl, propoxycarbonyl, isopropoxycarbonyl, butoxycarbonyl, isobutoxycarbonyl, sec-butoxycarbonyl, pentyloxycarbonyl, isopentyloxycarbonyl, neopentyloxycarbonyl, tert-pentyloxycarbonyl, hexyloxycarbonyl, mono- or dimethylcarbamoyl, mono- or diethylcarbamoyl, mono- or dipropylcarbamoyl, mono- or diisopropylcarbamoyl, mono- or dibutylcarbamoyl, mono- or dipentylcarbamoyl, mono- or dihexylcarbamoyl or N-methyl-N-ethylcarbamoyl.

X, $L^1$ and $L^2$ are e.g. $CH_2$, $(CH_2)_2$, $(CH_2)_3$, $(CH_2)_4$, $CH(CH_3)CH_2$ or $CH(CH_3)$ $CH(CH_3)$.

X is furthermore e.g. $(CH_2)_5$, $(CH_2)_6$, $(CH_2)_7$, $(CH_2)_8$, $C_2H_4$—O—$C_2H_4$, $C_2H_4$—NH—$C_2H_4$, $C_2H_4$—N($CH_3$)—$C_2H_4$, $C_2H_4$—O—$C_2H_4$—O—$C_2H_4$, $C_2H_4$—NH—$C_2H_4$—NH—$C_2H_4$, $C_2H_4$—N($CH_3$)—$C_2H_4$—N($CH_3$)—$C_2H_4$, $C_2H_4$—O—$C_2H_4$—N($CH_3$)—$C_2H_4$, $C_2H_4$—O—$C_2H_4$—O—$C_2H_4$—O—$C_2H_4$ $C_2H_4$—NH—$C_2H_4$—NH—$C_2H_4$—NH—$C_2H_4$, $C_2H_4$—N($CH_3$)—$C_2H_4$—N($CH_3$)—$C_2H_4$—N($CH_3$)—$C_2H_4$, $C_2H_4$—CO—NH—$C_2H_4$, $C_2H_4$—CO—NH—$C_3H_6$, $C_3H_6$—CO—NH—$C_2H_4$, $C_2H_4$—CO—NH—$C_3H_6$, $C_3H_6$—CO—NH—$C_3H_6$ or $C_3H_6$—CO—N($CH_3$)—$C_3H_6$.

Q is hydroxyl or a group which can be removed under alkaline reaction conditions. Such groups are e.g. chlorine, bromine, $C_1$-$C_4$-alkylsulfonyl, phenylsulfonyl, $OSO_3H$, $SSO_3H$, $OP(O)(OH)_2$, $C_1$-$C_4$-alkylsulfonyloxy, phenylsulfonyloxy, $C_1$-$C_4$-alkanoyloxy, $C_1$-$C_4$-dialkylamino or a radical of the formula

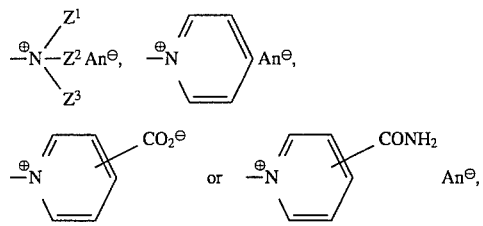

where $Z^1$, $Z^2$ and $Z^3$ are identical or different and independently of one another in each case have the meaning of $C_1$-$C_4$-alkyl or benzyl and An$\ominus$ in each case has the meaning of an equivalent of an anion. Suitable anions here are e.g. fluoride, chloride, bromide, iodide, mono-, di- or trichloroacetate, methanesulfonate, benzenesulfonate or 2- or 4-toluenesulfonate.

Preferred sulfur compounds of the formula I are those where A is methylene, carbonyl or the radical of the formula $CH_2$—CO.

Preferred sulfur compounds of the formula I are furthermore those where X is $C_1$-$C_8$-alkylene which may be interrupted by 1 to 3 oxygen atoms in ether linkage.

Preferred sulfur compounds of the formula I are furthermore those where $R^1$ is hydrogen or amino and $R^2$ is hydrogen.

Preferred sulfur compounds of the formula I are furthermore those where n is 2.

Particularly preferred sulfur compounds of the formula I are those where A is methylene.

Particularly preferred sulfur compounds of the formula I are furthermore those where $R^1$ is amino and $R^2$ is hydrogen.

The novel sulfur compounds of the formula I can be obtained in a manner known per se. For example, a benzene derivative of the formula II

where $R^1$, $R^2$ and A in each case have the abovementioned meanings, can be reacted with an amine of the formula III

where n, X and Y in each case have the abovementioned meanings.

An advantageous procedure is the reaction of the benzene derivatives of the formula II first with a thioether of the formula IIIa

where X and Y in each case have the abovementioned meanings, and subsequent oxidation of the sulfide to the sulfonyl group, e.g. using hydrogen peroxide.

$R^1$ and $R^2$, if they are different from hydrogen, can also be subsequently introduced into the benzene ring by a route known per se. In particular when introducing the hydroxysulfonyl group or the nitro group, which can then be reduced to the amino group, this route is preferred.

The novel sulfur compounds of the formula I are useful intermediates for the preparation of dyestuffs, in particular of reactive dyestuffs.

The following examples are intended to illustrate the invention in greater detail.

EXAMPLE 1

A mixture of 302 g of 2-aminoethyl-2'-hydroxyethyl sulfide and 268 g of phthalide was heated at from 220° to 225° C. for 3 h. After cooling, 250 ml of water were added and the pH was adjusted to 6.5 using sulfuric acid. After addition of 1 g of tungstic acid, 680 g of 30% strength by weight aqueous hydrogen peroxide solution were added dropwise at from 65° to 80° C. in the course of 1 h. After cooling, the precipitate was filtered off with suction and dried. 407 g of the compound of the formula

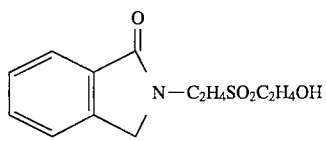

were isolated.
M.p.: 172° to 174° C.
NMR (D6-DMSO): 3.31 (m, 2), 3.52 (m, 2), 3.81 (m, 2), 4.00 (m, 2), 4.55 (s, 2), 5.20 (t,1), 7.5–7.7 (m, 4).

EXAMPLE 2

174 g of the compound from Example 1 were introduced with cooling into 600 g of 96% strength by weight sulfuric acid and the mixture was stirred at room temperature for 8 h. After cooling to from 0° to 5° C., 34.7 g of 100% strength by weight nitric acid in 70 g of 96% strength by weight sulfuric acid were added in the course of 3 h. After a further 3 h, the mixture was diluted with ice, the pH was adjusted to 0.2 to 0.3 using solid sodium hydrogen carbonate and the precipitate was filtered off with suction. 240 g of the compound of the formula

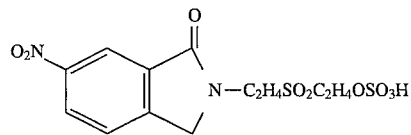

were isolated in the form of a moist press cake.
M.p.: 154° to 157° C. (from butanol).

EXAMPLE 3

240 g of the moist press cake from Example 2 were dissolved in 700 ml of water, the pH was adjusted to 4.5 using sodium acetate and hydrogen gas was introduced at from 50° to 55° C. in the presence of 5 g of a palladium catalyst. After absorption of hydrogen was complete, the catalyst was filtered off and the filtrate concentrated under reduced pressure. 177 g of a compound of the formula

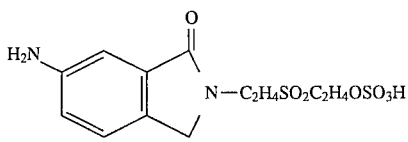

were isolated after drying.
Content determination by diazotization: 69%.
NMR (D6-DMSO): 3.50 (m, 4), 3.92 (m, 2), 4.12 (m, 2), 4.38 (s, 2), 5.30 (s, 2), 6.8 (m, 2), 7.2 (d, 1)

EXAMPLE 4

A solution of 69 g of the compound from Example 3 in 500 ml of water was adjusted to a pH of 10 at from 25° to 30° C. using sodium carbonate. An oil deposited which slowly crystallized. The crystals were filtered off with suction and after drying 42 g of the compound

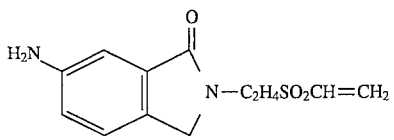

were isolated.
M.p.: 144° to 148° C.
NMR ($D_6$-DMSO): 3.55 (m, 2), 3.88 (m, 2), 4.35 (s, 2), 5.38 (s, 2), 6.3 (m, 2), 6.85 (m, 2), 7.02 (m, 1), 7.21 (d, 1)

EXAMPLE 5

135 g of the compound from Example 1 were stirred in 500 g of xylene and treated slowly with 119 g of thionyl chloride at from 65° to 68° C. After a further 3 h at from 65° to 68° C., the mixture was cooled and the precipitate was filtered off with suction. After drying, 144 g of the compound of the formula

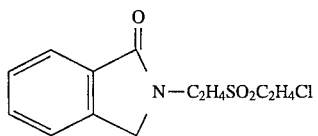

were isolated.
M.p.: 162° to 164° C.
The procedure was then as described in Examples 2 and 3 and the compound of the formula

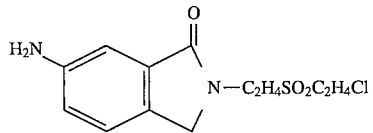

was obtained.
M.p.: 169° to 171° C.

EXAMPLE 6

The procedure was as described in Example 1, but the phthalide was replaced by 296 g of phthalic anhydride. 410 g of the compound of the formula

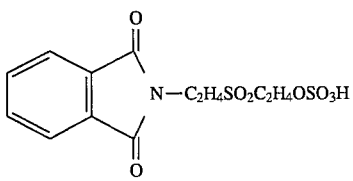

were obtained.

M.p.: 126° to 130° C.

The procedure was then as described in Examples 2 and 3 and the compound of the formula

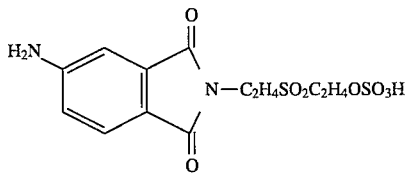

was obtained.

NMR ($D_6$-DMSO): 3.45 (m, 4), 3.95 (t, 2), 4.10 (t, 2), 6.5 (s, 2), 6.80 (dd, 1), 6.95 (s, 1), 7.50 (d, 1)

EXAMPLE 7

The compound from Example 6 was reacted in a similar manner to Example 4. The compound of the formula

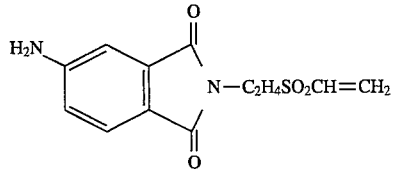

was thus obtained.

M.p.: 143° to 145° C.

EXAMPLE 8

Homophthalic anhydride was reacted with 2-aminoethyl-2'-hydroxyethyl sulfide as described in Example 1 and the oil obtained was oxidized using 30% strength by weight aqueous hydrogen peroxide. The compound of the formula

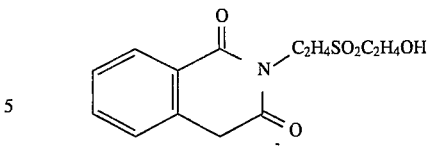

was thus isolated.

M.p.: 146° to 149° C.

NMR ($D_6$-DMSO): 3.4 (m, 4), 3.80 (m, 2), 4.15 (s, 2), 4.30 (m, 2), 5.21 (t, 1), 7.41 (m, 1), 7.50 (m, 1), 7.68 (m, 1), 8.08 (m, 1)

We claim:

1. A sulfur compound of the formula I

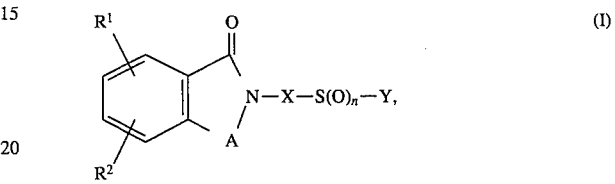

where n is 0 or 2, $R^1$ and $R^2$ independently of one another in each case are hydrogen, $C_1$–$C_6$-alkyl, $C_1$–$C_6$-alkoxy, halogen, nitro, amino, hydroxysulfonyl, $C_1$–$C_6$-alkoxycarbonyl, carbamoyl or $C_1$–$C_6$-mono- or dialkylcarbamoyl, A is methylene, carbonyl, sulfonyl or a radical of the formula $CH_2$—CO or $CH_2$—$SO_2$, the methylene group in each case being linked to the benzene ring, X is a direct bond, $C_1$–$C_8$-alkylene which may be interrupted by 1 to 3 oxygen atoms in ether linkage, 1 to 3 imino groups or 1 to 3 $C_1$–$C_4$-alkylimino groups, or a radical of the formula $L^1$—CO—$NR^3$—$L^2$, where $L^1$ and $L^2$ independently of one another in each case are $C_1$–$C_4$-alkylene and $R^3$ is hydrogen, $C_1$–$C_4$-alkyl or phenyl, and Y is vinyl or a radical of the formula $C_2H_4Q$, where Q is hydroxyl or a group which can be removed under alkaline reaction conditions.

2. A sulfur compound as claimed in claim 1, wherein A is methylene, carbonyl or the radical of the formula $CH_2$—CO.

3. A sulfur compound as claimed in claim 1, wherein X is $C_1$–$C_8$-alkylene which may be interrupted by 1 to 3 oxygen atoms in ether linkage.

4. A sulfur compound as claimed in claim 1, wherein $R^1$ is hydrogen or amino and $R^2$ is hydrogen.

* * * * *